(12) United States Patent
Odderson (10) Patent No.: US 7,496,407 B2
(45) Date of Patent: Feb. 24, 2009

(54) NERVE STIMULATOR MEASURING DEVICE

(76) Inventor: Ib R. Odderson, 9319 NE. 135TH La., Kirkland, WA (US) 98034

( * ) Notice: Subject to any disclaimer, the term of this patent is extended or adjusted under 35 U.S.C. 154(b) by 0 days.

(21) Appl. No.: 11/021,299

(22) Filed: Dec. 23, 2004

(65) Prior Publication Data

US 2005/0148898 A1    Jul. 7, 2005

Related U.S. Application Data

(60) Provisional application No. 60/541,511, filed on Feb. 3, 2004, provisional application No. 60/532,029, filed on Dec. 23, 2003.

(51) Int. Cl.
*A61N 1/02* (2006.01)
(52) U.S. Cl. .............................. 607/60; 33/760; 33/761; 600/384; 600/554
(58) Field of Classification Search .................. 607/60; 600/384, 554; 33/755
See application file for complete search history.

(56) References Cited

U.S. PATENT DOCUMENTS

| 740,943 | A | | 10/1903 | Summersby et al. |
|---|---|---|---|---|
| 766,911 | A | | 8/1904 | Stemm |
| 4,807,643 | A | | 2/1989 | Rosier ........................ 128/741 |
| 4,875,296 | A | | 10/1989 | Holzmeister et al. .......... 33/770 |
| 5,301,683 | A | | 4/1994 | Durkan ....................... 128/744 |
| 5,327,902 | A | * | 7/1994 | Lemmen ..................... 600/547 |
| 6,178,652 | B1 | | 1/2001 | Foster .......................... 33/511 |

* cited by examiner

*Primary Examiner*—Mark W Bockelman
*Assistant Examiner*—Eric D Bertram
(74) *Attorney, Agent, or Firm*—Dean A. Craine (57) ABSTRACT

A nerve stimulator measuring device used to measure the length of electrical conduction of a nerve using a standard electrical nerve stimulator. The device includes an outer housing attached or integrally formed on the cathode probe on the standard nerve stimulator. Mounted on the two probes or located inside the outer housing is a retractable, flexible tape measure with length measure units printed thereon. During assembly, the outer housing is positioned over the two probes so that the tape measure disposed therebetween. During use, the end point of the tape is positioned over the recording sensor. The nerve stimulator is then pulled towards the hand so that the tape unwinds to the display the desired distance. The nerve stimulator is then held so that the cathode probe is pressed against the skin over the nerve and adjacent to the desired distance shown on the tape. The nerve stimulator is then activated and a reading is obtained.

10 Claims, 7 Drawing Sheets

NERVE STIMULATOR MEASURING DEVICE

This utility patent application is based on the provisional patent application (Ser. No. 60/532,029) filed on Dec. 23, 2003, and the provisional patent application (Ser. No. 60/541,511) filed on Feb. 3, 2004.

BACKGROUND OF THE INVENTION

1. Field of the Invention

This invention relates to devices used to measure nerve conduction in peripheral nerves and more particularly, to such devices that measure the conduction time and amplitude of a test signal applied to a nerve.

2. Description of the Related Art

It is common practice in medicine to measure the electrical conduction on a peripheral nerve. For example, when diagnosing carpel tunnel syndrome it is common for a physician to measure the electrical conduction in the median nerve as it extends from the forearm, through the wrist and into the hand. During the test procedure, the physician measures the length of time and the amplitude of a test signal applied to the nerve having a known length. To perform the test, recording sensors are attached to the patient's forearm and a nerve stimulator is positioned over the nerve.

When testing for carpel tunnel syndrome, the recording sensors and the nerve stimulator's cathode probe must be spaced apart at selected distances (8 cm, 10 cm, and 14 cm) on the hand and forearm. Heretofore, physicians have used a ruler or measuring tape and an ink marker to first mark the specific locations of the recording electrodes and the nerve stimulator on the patient's skin before the test is performed. Often, several tests are performed on the same hand and forearm during the visit, which requires manually marking the skin reference points. The act of measuring and marking several sets of reference points on the forearm and hand is very time consuming. Also, because the sets of reference points are relatively close, a wrong set of reference points may be used during the test that produces inaccurate readings.

SUMMARY OF THE INVENTION

It is an object of the present invention to provide a nerve stimulator measuring device that enables a physician to easily and quickly determine the proper position of the nerve stimulator.

It is another object of the invention to provide such a device that may be used with a standard electrical nerve stimulator that uses a cathode probe and an anode probe that are positioned against or adjacent to the skin.

It is another object of the invention to provide such a device that enables a physician to determine different locations of the cathode probe from the electrical sensor without using an ink marker.

It is another object of the invention to provide such a device that is wireless thereby eliminating wires that typically extend from the device to the recording machine.

These and other objects are met by the nerve stimulator measuring device with a tape measure attached thereto used to measure the distance between the electrical sensor and the cathode probe. In the first embodiment, the tape measure is located in an outer housing that attaches or is integrally formed on the cathode probe on a standard electrical nerve stimulator. The outer housing includes two bores designed to receive the anode and cathode probes on the electrical nerve stimulator. During assembly, the outer housing is positioned over the two probes with the tape measure disposed therebetween. An index marking or line formed on the outer surface of the outer housing is aligned with the center axis on the cathode probe.

In a second embodiment, the device comprises an outer housing with a tape receiver cavity formed therein that holds a spool upon which a flexible tape measure is wound and unwound. The spool is coupled to a tape retraction mechanism that automatically rewinds the tape measure on the spool. Mounted on the outer surface of the outer housing is a stimulator activation button coupled to an electric test signal generator and a tape retraction button coupled to the tape retraction mechanism.

In the second embodiment, disposed on the distal end of the tape measure used with the second embodiment, are three recording sensors. Wires extend from the three recording sensors to an optional wireless transmitter located inside the outer housing. During operation, the wireless transmitter transmits the detected electrical signal information from the sensors to a wireless receiver connected to a nearby recording machine. The three wires that connect to the three recording sensors are mounted on the tape measure and are extended and retracted into the outer housing with the tape measure. Also mounted on the outer housing is a signal intensity control switch that the user manually operates to adjust the size of the signal generated by the stimulator probes.

When the first embodiment is used to diagnose carpel tunnel syndrome, the recording sensors are first attached to the forearm over the median nerve. The free end of the tape measure is then centrally aligned over the first recording sensor and the electrical stimulator with the outer housing attached thereto is pulled towards the hand to the desired length (8 cm, 10 cm, or 14 cm) required for the test. The electrical nerve stimulator is then held so that the cathode probe is aligned on the skin adjacent to the desired distance on the tape. The electrical nerve stimulator is then activated and a reading is obtained. When additional tests are to be conducted, the recording sensor is again used as a reference point for the free end of the tape. The electric nerve stimulator is moved to the new testing point so that the desired distance is displayed on the tape. The electrical nerve stimulator is then held so that the cathode probe is then pressed against the skin adjacent to the new distance.

When the second embodiment is used to diagnose carpel tunnel syndrome, the end of the tape measure is pulled from the outer housing so that the three electrical sensors are longitudinally aligned at a desired location of a desired nerve on the forearm. The outer housing is then pulled towards the hand so that the anode and cathode stimulator prongs are positioned at a desired location (8 cm, 10 cm, or 14 cm) on the tape measure. The stimulator button is then pressed to activate the electrical nerve stimulator. The optional signal intensity switch is used to adjust the desired signal intensity. When additional tests are to be conducted, the nerve sensor probes are moved to a new location on the tape measure and the stimulator button is activated. When the test is completed the tape retraction button is activated to automatically retract the tape measure into the outer housing.

DESCRIPTION OF THE PREFERRED EMBODIMENT(S)

Shown in the accompanying FIGS. 1-19, are four embodiments of an electrical nerve stimulator measuring device, denoted 10, 10', 10" 10''', used to measure the distance of conductivity in a peripheral nerve. Referring to the first embodiment shown in FIGS. 1, 3, and 4, the device 10 comprises an outer housing 20 with two side ears 11, 12 that attach to the anode and cathode probes 78, 80, respectively, on a handheld electrical nerve stimulator 70.

Figure 1:
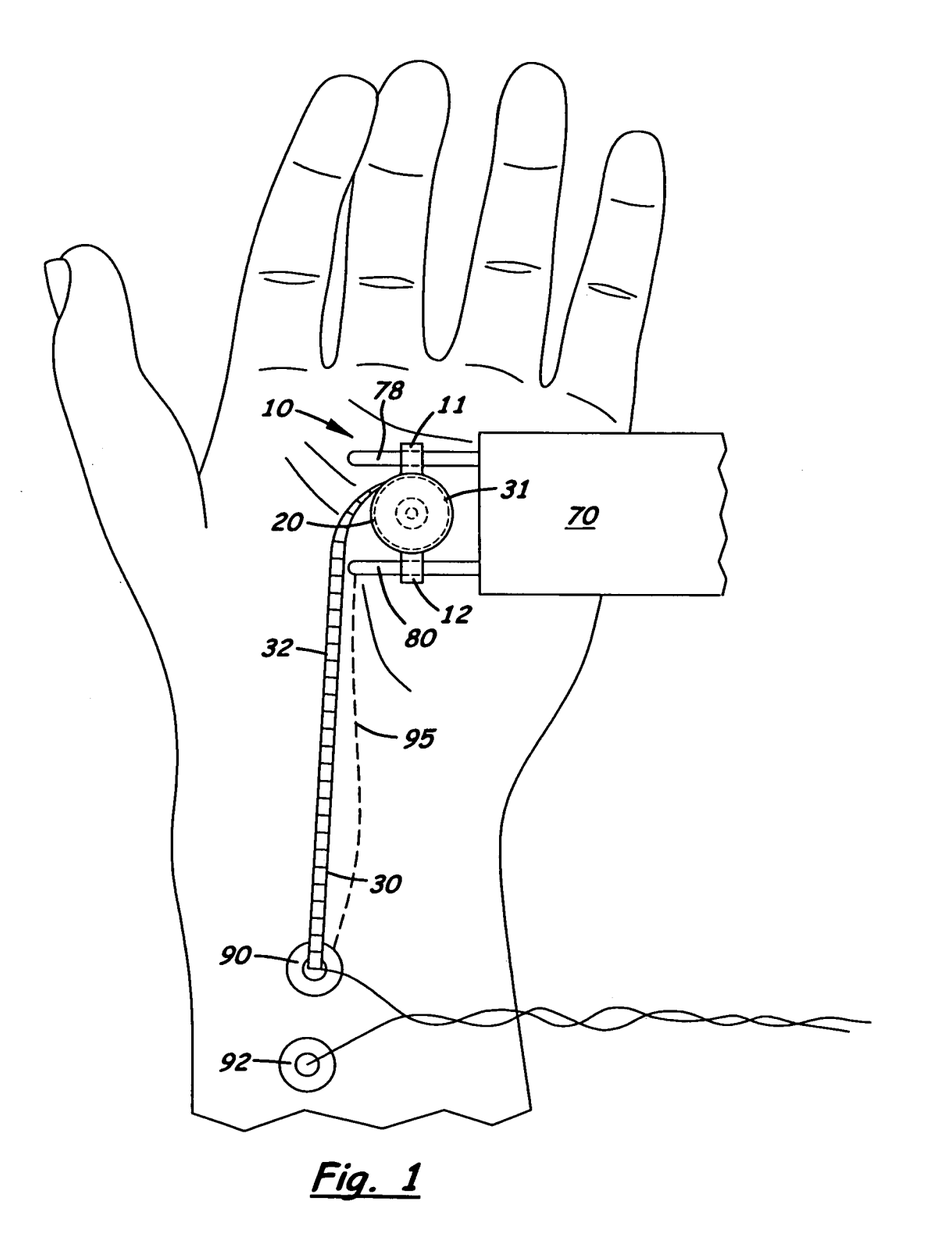
FIG. 1 is a perspective view of the first embodiment of the nerve stimulator measuring device disclosed herein.
Figure 3:
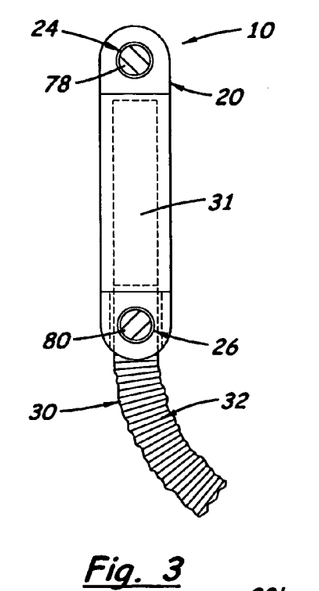
FIG. 3 is a top plan view of the first embodiment of the nerve stimulator measuring device shown in FIG. 1.
Figure 4:
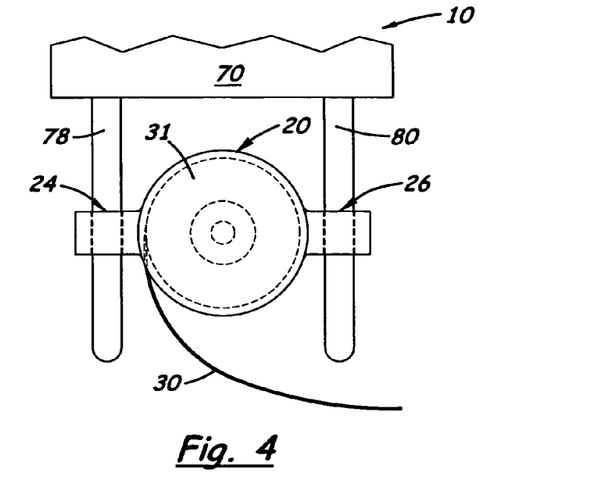
FIG. 4 is a side elevational view of the first embodiment of the nerve stimulator measuring device shown in FIGS. 1 and 3.

Located inside the outer housing 20 is a retractable spool 31 with a flexible tape 30 with length measure units 32 printed thereon. In the preferred embodiment, the two ears 11, 12 include two bores 24, 26 designed to slidingly receive the anode and cathode probes, 78, 80 respectively. The outer housing 20 is aligned on the probes 78, 80 so that the tape measure 30 unwinds around a center axis that is perpendicular to the longitudinal axis of the two probes 78, 80.

Figure 2:
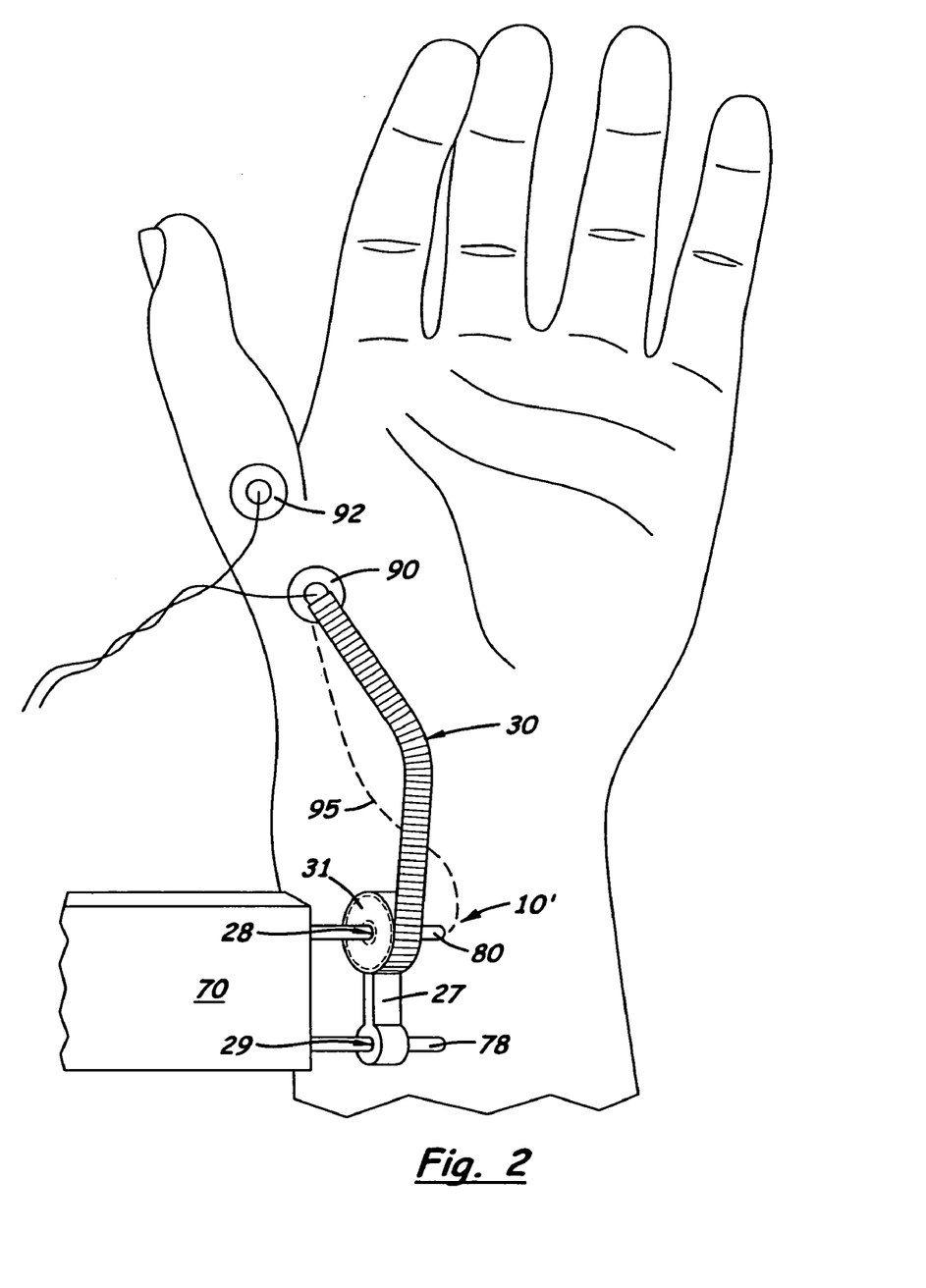
FIG. 2 is a side elevational view of another embodiment of the nerve stimulator measuring device.
Figure 5:
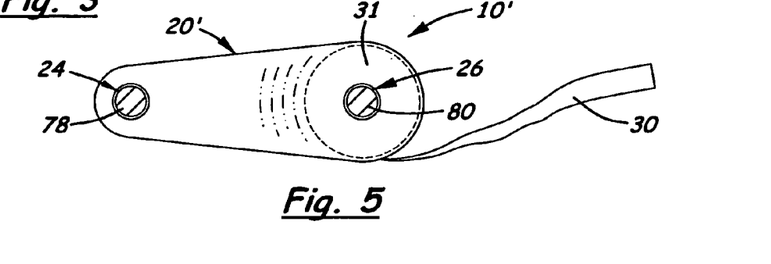
FIG. 5 is a top plan view of the second embodiment of the nerve stimulator measuring device shown in FIG. 2.
Figure 6:
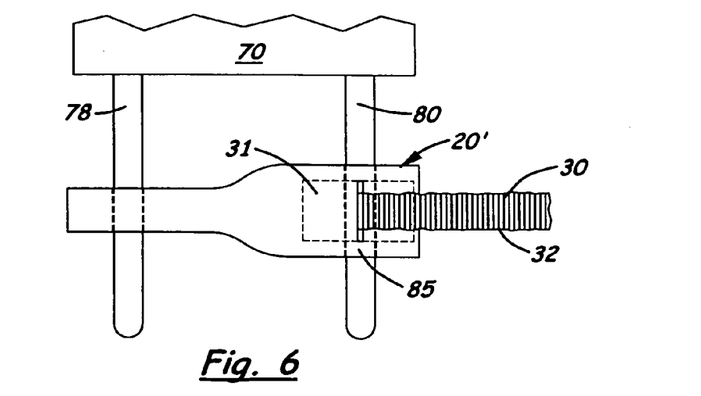
FIG. 6 is a side elevational view of the second embodiment of the nerve stimulator measuring shown in FIGS. 2 and 5.

The second embodiment of the device 10', shown in FIGS. 2, 5 and 6, comprises the tape measure 30 also disposed inside an outer housing 20' designed to be coaxially aligned around the cathode probe 80. The outer housing 20' includes a center bore 28 that receives the cathode probe 80 on the electrical nerve stimulator 70. A portion 27 of the outer housing 20' extends laterally and includes a second bore 29 designed to slidingly receive the anode probe 78. The spool 31 for the tape measure 30 is aligned inside the outer housing 20' so that it unwinds around a center axis coaxially aligned with the cathode probe 80. When properly assembled on the electrical nerve stimulator 70, the anode probe 78 extends through the second bore 29 and prevents the outer housing 20' from rotating on the stimulator 70.

Figures 7, 8, 9, 10:
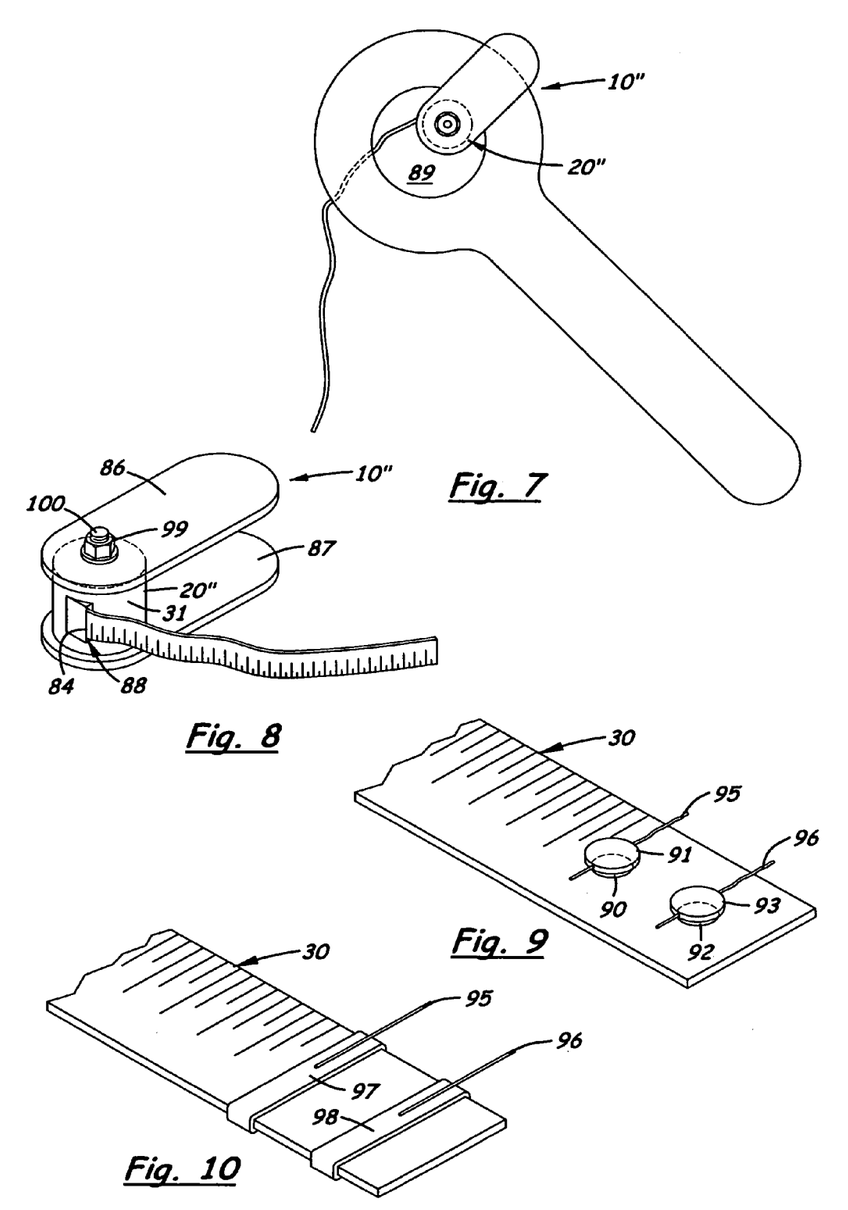
FIG. 7 is a perspective view of a third embodiment of the nerve stimulator measuring device used with a magnetic nerve stimulator.
FIG. 8 is a second perspective view of the third embodiment of an electromagnetic nerve stimulator measuring device shown in FIG. 7.
FIG. 9 is a perspective view of two tab sensors directly connected to the distal end of tape.
FIG. 10 is a perspective view of the distal end of the tape with two wrap sensors attached thereto.

FIGS. 7 and 8 show a third embodiment of the measuring device, denoted 10", designed to be used with a electromagnetic nerve stimulator 85. Device 10" comprises two clamping members 86, 87 located on the opposite sides of a cylindrical shaped outer housing 20". Like the first two embodiments, located inside the outer housing 20" is a retractable spool 31 with a flexible tape measure 30 wound thereon. Formed on the side of the outer housing 20" is an exit port 88 through which the distal end of the tape measures 30 extends. The two clamping members 86, 87 are designed to extend and adjustably squeeze around the circular body of the magnetic electrical nerve stimulator 85. A threaded bolt 100 and nut 99 are used to apply a clamping force to the two clamping members 86, 87. The outer housing 20 is aligned on the two clamping members 86, 87 to that its center axis is perpendicular to the longitudinal axis on the two clamping members 86, 87. When properly assembled, the exit port 88 is aligned over the center axis of the center opening 89 on the electro-magnetic nerve stimulator 85.

In the first three embodiments 10, 10', 10", an optional index marking or surface 84 may be printed or formed on the outer body 20, 20', or 20" that denotes the reference point for the tape measure 30.

As shown in FIGS. 1 and 2, during use, the two recording sensors 90, 92 are positioned on the skin over or proximal end of the nerve 95. The end of the tape measure 30 is then grasped and aligned with the center axis of the first recording sensor 90. The electrical nerve stimulator 70 is then pulled toward the hand to unwind the tape measure 30 from the outer housing 20, 20'. Using the index mark on the outer housing 20 and the length measurement units 32 on the tape measure 30, the electrical nerve stimulator 70 is then positioned so that its cathode probe 80 is placed at the desired location on the skin over the nerve 95 and adjacent to the desired distance shown on the tape measure 30. The electrical nerve stimulator 70 is then activated and a reading is obtained. When additional tests are to be conducted, the first recording sensor 90 is used as a reference point, and the tape measure 30 unwound from the outer housing 20 until the desired length is indicated. The electrical nerve stimulator 70 is then selected and the cathode probe 80 is then aligned over the skin adjacent to the new desired distance.

When using the third embodiment of the device 10", the electro-magnetic stimulator 85 is held so that the center axis of the central opening 89 is longitudinally aligned over the nerve 95. The stimulator 85 is held so that the exit port 88 of the device 10" is positioned directly over the nerve 95. The end of the tape measure 30 is then pulled and positioned over the sensor. The distance indicia on the tape measure 30 at the exit port 88 or surface 84 is then read. With devices 10, 10', and 10", the recording sensors 90 and 92 may be attached or formed in the distal end of the tape measure 30. As shown in FIG. 9, the recording sensors 90, 92 may be "button-like" tab connectors 91, 93, respectively, that connect to the lead wires 95, 96 that connect to the recording machine. In FIG. 10, the connectors 91, 93 are replaced with two strap connectors 97, 98, respectively, that wrap around tape measure 30 and connect to lead wires 95, respectively.

Figure 11:
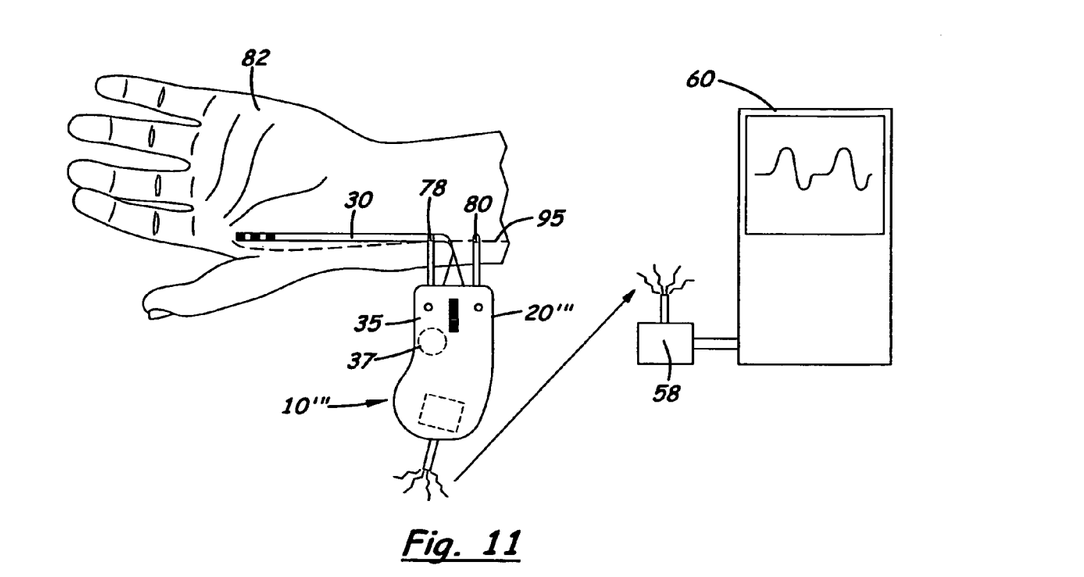
FIG. 11 is an illustration showing a fourth embodiment of the nerve stimulator measuring deviceused to measure the conductivity of a nerve on a patent's hand.
Figure 12:
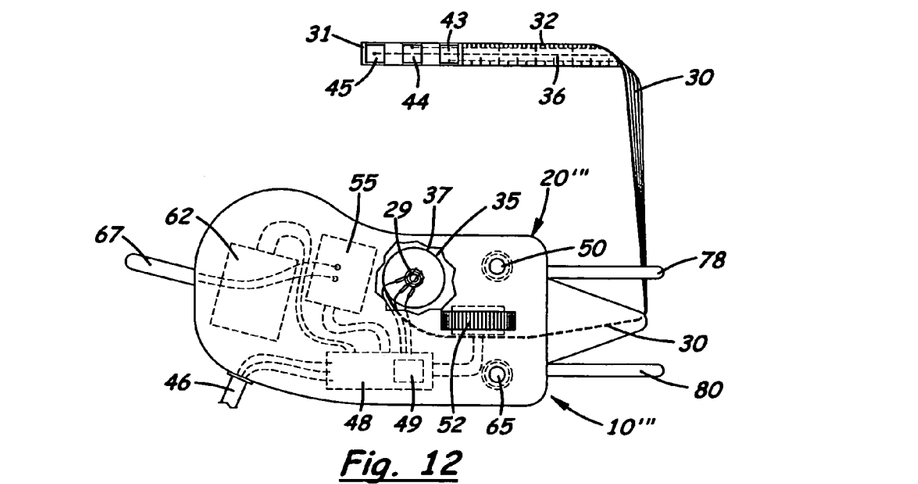
FIG. 12 is a top plan view of the fourth embodiment of nerve stimulator measuring device.
Figure 13:
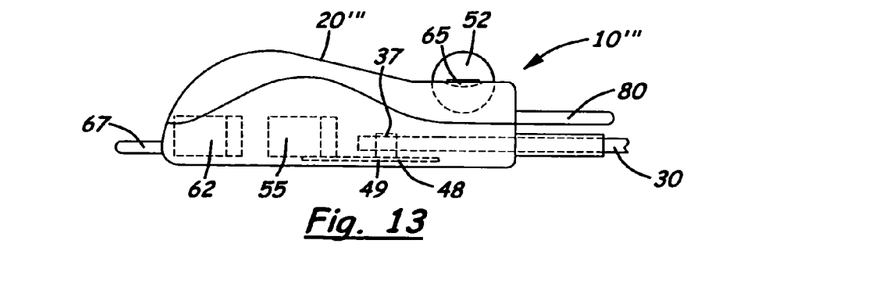
FIG. 13 is a right side elevational view of the fourth embodiment of the nerve stimulator measuring device shown in FIGS. 11 and 12.
Figure 14:
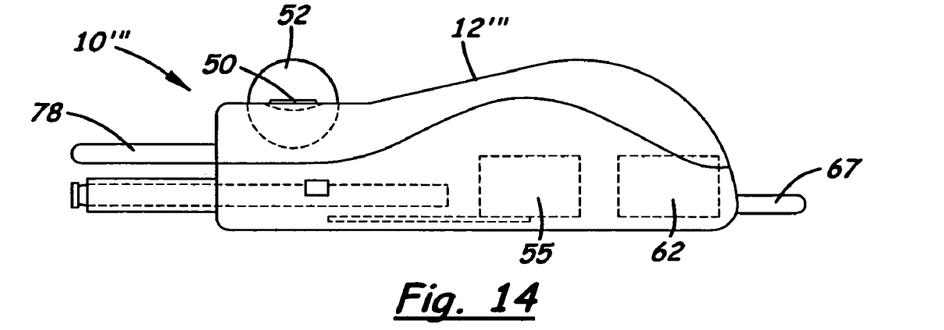
FIG. 14 is a left side elevational view of the nerve stimulator measuring device shown in FIGS. 11-13.
Figure 15:
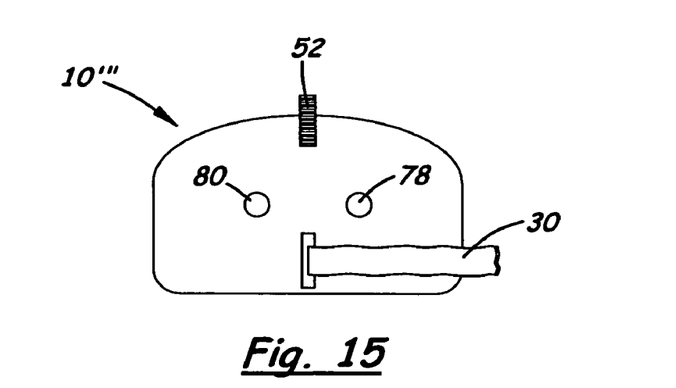
FIG. 15 is a front elevational view of the nerve stimulator measuring device shown FIGS. 11-14.
Figure 16:
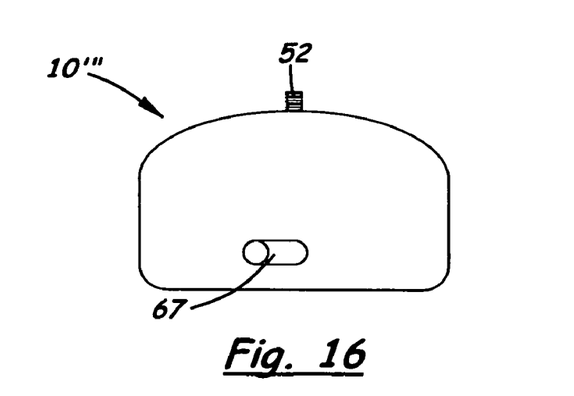
FIG. 16 is a rear elevational view of the nerve stimulator measuring shown in FIGS. 11-15.
Figure 17:
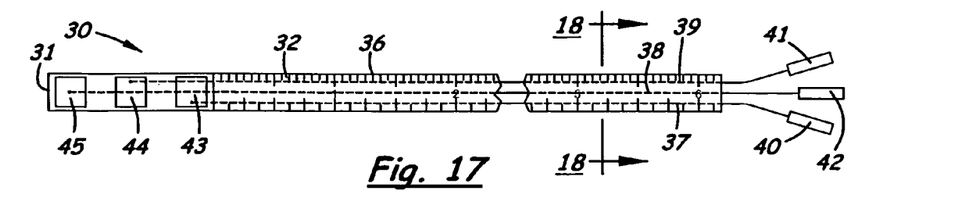
FIG. 17 is a top plan view of a third embodiment of the tape measure.
Figure 18:
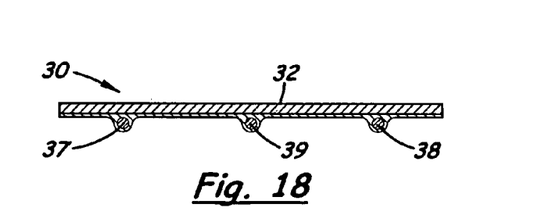
FIG. 18 is a sectional view taken along line 18-18 FIG. 17.
Figure 19:
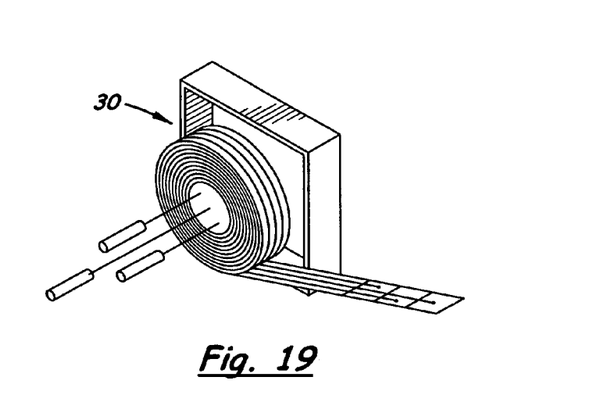
FIG. 19 is a perspective view of tape measure shown in FIGS. 17 and 18 rolled onto a spool.

Shown in the accompanying FIGS. 11-18, is a fourth embodiment of the device, denoted 10''' also used to measure the distance of conductivity in a peripheral nerve 95. Referring to FIGS. 11, 13, and 14, the device 10''' comprises an outer housing 20''' with an anode and cathode probes 78, 80, respectively, longitudinally aligned and extending from one end. Mounted inside the outer housing 20''' is a tape measure receiver cavity 35 that holds a spool 37 and a tape retraction mechanism (not shown) that automatically rewinds the tape measure 30 onto the spool 37.

The three recording sensors 43, 44, 45 are mounted longitudinally near the distal end 31 of the tape measure 30. Printed on the front surface 32 of the tape measure 30 are metric or English distance markings 36 that enable the user to determine the distance from the closest recording sensor. Also mounted on the outer surface of the outer housing 20''' is a tape retraction button 65 coupled to the tape retraction mechanism 39 which when activated, automatically retracts the tape measure 30 into the outer housing 12.

As shown in FIG. 12, an electric test signal generator 49 is mounted on a printed circuit board 48 disposed inside the outer housing 12'''. Wires from the two prong stimulators 78, 80 connect to a printed circuit board 48. During operation, the test signal generator 49 produces a test signal to the two prong stimulators 78, 80. It should be understood, however, that the electrical test signal generator 49 may be eliminated from the outer housing 20''' and mounted in an external device (not shown) that is connected to the outer housing 20''' via a cable 67. Also mounted on the outer surface of the outer housing 20''' is a stimulator activation button 50 coupled to the electric test signal generator 49. A test single intensity dial 52 is also provided to allow the user to adjust the intensity of the test signal.

Located inside the outer housing 20''' is an optional wireless transmitter 55 connected printed circuit board 48. During operation, the wireless transmitter 55 transmits detected electrical signal information from three sensors 43, 44, 45 to a wireless receiver 58 connected to a nearby recording machine 60 shown in FIG. 11. When the wireless transmitter 55 is not provided in the device, the three wires connect directly to main cable 46 that runs to the recording machine 60. Located inside the outer housing 20''' is a 9 volt battery 62 that provides electricity to the probes 78, 80 and to the printed circuit board 48.

When device 10''' is used to diagnose carpel tunnel syndrome, the distal end 31 of the tape measure 30 is pulled from the outer housing 12 so that the three electrical sensors 43, 44, 45 are aligned at the desired location on the hand 82. The outer housing 20''' is then pulled so that the anode and cathode stimulator prongs 78, 80 are positioned at a desired location (8 cm, 10 cm, or 14 cm) on the tape measure 30 along the forearm. The stimulator button 50 is then pressed to activate the electrical test signal generator 49. The optional signal density dial 52 is used to adjust the signal intensity. When additional tests are to be conducted, the nerve sensor probes 78, 80 are moved to a new location on the tape measure 30 and the stimulator button 50 is activated. When the test is completed the tape retraction button 65 is activated to automatically retract the tape measure 30 into the outer housing 20'''.

In compliance with the statute, the invention described herein has been described in language more or less specific as to structural features. It should be understood, however, that the invention is not limited to the specific features shown, since the means and construction shown is comprised only of the preferred embodiments for putting the invention into effect. The invention is therefore claimed in any of its forms or modifications within the legitimate and valid scope of the amended claims, appropriately interpreted in accordance with the doctrine of equivalents.

I claim:

1. A nerve conducting testing and measuring system, comprising:
   a. a handheld nerve stimulator that includes an elongated body, an anode probe and a cathode probe longitudinally aligned and extending from one-end of said body;
   b. a retractable flexible tape measure with measurement units printed thereon, said tape measure being located inside an outer housing attached to said probes so that when the distal end of said tape measure is extended from said outer housing, the distance from said outer housing to a remote sensor can be measured;
   c. means for automatically retracting said tape measure inside said outer housing; and,
   d. an electric nerve signal generator connected to said anode probe and said cathode probe on said handheld nerve simulator.

2. The system as recited in claim 1, wherein said tape measure includes at least one recording sensor located at the distal end thereof.

3. The system as recited in claim 2, further includes a wireless transmitter capable of broadcasting a signal to a remote wireless receiver connected to a recording device.

4. The system as recited in claim 1, wherein said tape measure includes three recording sensors located near the distal end thereof.

5. The system as recited in claim 1, further includes a wireless transmitter capable of broadcasting a signal to a remote wireless receiver connected to a recording device.

6. The system as recited in claim 1, further includes a wireless transmitter capable of broadcasting a signal to a remote wireless receiver connected to a recording device.

7. A nerve stimulator testing and measuring system, including:
   a. a handheld nerve stimulator that includes an elongated body with an anode probe and a cathode probe longitudinally aligned and extending from one end thereof;
   b. a retracting spool;
   c. a flexible tape measure wound onto said spool, said tape measure including measure index printed on one surface;
   d. means for attaching said spool to said anode and cathode probes so that said tape measure may be extended from said spool to a reference electrode when conducting a nerve conduction test to measure the distance from said spool to the reference electrode and,
   e. an electric nerve signal generator connected to said anode probe and said cathode probe on said handheld nerve simulator.

8. The measuring device as recited in claim 7, wherein said tape measure includes at least one recording sensor located at the distal end thereof.

9. The measuring device as recited in claim 7, further includes a wireless transmitter capable of broadcasting a signal to a remote wireless receiver connected to a recording device.

10. A handheld nerve stimulator testing and measuring system including:
    a. a nerve stimulator that includes and elongated body with an anode probe and a cathode probe longitudinally aligned and extending from one end;
    b. an outer housing mounted between said anode probe and said cathode probe, said outer housing includes an index marker that is aligned and registered with the center axis of said cathode probe;
    c. a retractable, flexible tape measure with length measure units printed thereon located inside said outer housing;
    d. an electric nerve signal generator connected to said anode probe and said cathode probe;

e. an anode recording sensor attached to the distal end of said tape measure;
f. a cathode recording sensor attached to the distal end of said tape measure; and,
g. a wireless transmitter connected to said anode recording sensor and said cathode recording sensor.

* * * * *